United States Patent [19]
Porte

[11] Patent Number: 5,034,191
[45] Date of Patent: Jul. 23, 1991

[54] INCUBATOR AND ANALYZER WITH IMPROVED CAP RAISING MEANS

[75] Inventor: Johannes J. Porte, Webster, N.Y.

[73] Assignee: Eastman Kodak Company, Rochester, N.Y.

[21] Appl. No.: 293,718

[22] Filed: Jan. 5, 1989

[51] Int. Cl.$^5$ .............................................. G01N 35/04
[52] U.S. Cl. ....................................... 422/64; 422/63; 436/46
[58] Field of Search ....................... 422/63, 64; 436/46

[56] References Cited

U.S. PATENT DOCUMENTS 4,053,381 10/1977 Hamblen et al. .
4,273,639 6/1981 Gottermeier .
4,298,571 11/1981 DiFulvio et al. .
4,844,872 7/1989 Geiselman et al. .................... 422/63

FOREIGN PATENT DOCUMENTS 0287005 10/1988 European Pat. Off. .............. 436/46

Primary Examiner—Robert J. Warden
Assistant Examiner—D. John Griffith, Jr.
Attorney, Agent, or Firm—Dana M. Schmidt

[57] ABSTRACT

There are described an incubator and an analyzer using such, in which the evaporation caps of the test element holding means are caused to be raised at loading and unloading stations by a fixed camming surface and a cam follower on each of the caps. As a result, size and complexity of the incubator are substantially reduced.

6 Claims, 3 Drawing Sheets

INCUBATOR AND ANALYZER WITH IMPROVED CAP RAISING MEANS

FIELD OF THE INVENTION

This invention relates to the field of incubators of test elements, particularly those used in analyzers, and means for allowing proper loading and unloading of test elements into and from such incubators.

BACKGROUND OF THE INVENTION

Incubators of test elements provide a key function of maintaining the temperature of the test element and the liquid contained therein, at a desired level, usually an elevated level. The purpose is to render the reaction of the liquid with the reagents of the test element, predictable. Predictability in turn requires that the same temperature be used, more or less, during the several minutes that the reaction needs to "cook". At the same time, a second function that the incubators provide is one of preventing evaporation of the contained liquid, since evaporation can change the amount of analyte being measured, for example, the amount of $CO_2$ being measured in a potentiometric test element. Because the temperature of the incubator is usually elevated, for example, at 37° C., evaporation will readily occur if the location of the liquid is not covered. Particularly this is true for potentiometric slides such as those described in U.S. Pat. Nos. 4,053,381 and 4,273,639, as in those cases, there is little room for the drops to be absorbed by the test element. That is, the drops tend to protrude above the top of the test element during the entire residence of the test element within the incubator.

Hence, most incubators are provided with evaporation caps, sometimes called covers. These need to seal onto the top of the test element when the latter is in place. Additionally, however, they need to be raised away from the test element as the latter enters into or is removed from the holding means of the incubator. Otherwise, the sealing edges of the cap will "wipe" the excess patient sample protruding above the test element, particularly the potentiometric test element, causing contamination.

One mechanism for effectively placing evaporation caps onto test elements, and for appropriately raising them, is shown in U.S. Pat. No. 4,298,571, FIG. 4. First, the cap has a beveled outside edge that an incoming test element strikes to start raising the cap, when such an element is entering the incubator. However, that alone is not enough to clear the cap from the liquid bubble of the test element, which can be seen in the Figure to protrude above the surface of the test element. In addition, there is provided a push rod that rises up from underneath to lift away the cap (which otherwise is biased against the held test element by spring 104, FIG. 3). That rod in turn is activated by a solenoid (112 in FIG. 4).

Such an incubator is very effective in the kind of large analyzer shown in the '571 patent. However, there has been a need for an incubator using simplified mechanisms, particularly one with a fewer number of active components such as solenoids and motors. Particularly such need is present on small, low-throughput analyzers such as are used in cramped quarters, for example, space stations. That is, the fewer the number of such active components, the smaller and more reliable the incubator can be. This is particularly the case when the cap lifting mechanism is the part that gives the incubator its greatest height, as is apparent from FIG. 5 of the '571 patent.

Analyzers used in space stations to monitor the health of astronauts have an additional constraint—the parts and test elements thereof must be kept confined lest they become floating objects that can be dangerous.

Therefore, prior to this invention there has been a need for an incubator that has means for raising and lowering evaporation caps, which are simplified and take up a minimum of space.

SUMMARY OF THE INVENTION

I have devised an incubator that solves the above-noted space problems and complexities of the prior art incubators.

More specifically, there is provided an incubator for test elements containing a liquid for analysis, the incubator including means defining a plurality of stations in the incubator, including at least one station providing a loading or an unloading function; holding means at each of the stations for holding a plurality of test elements, means for moving the holding means and the test elements through the stations; a plurality of movable evaporation caps disposed so that a cap is adjacent each of the stations, the caps being constructed to cover at least a portion of a test element at each station so as to prevent liquid evaporation, the caps including a spring mounted to bias the cap against a held test element; and means for raising the caps against the spring to allow entry or removal of a test element into or from the holding means. The incubator is improved in that the raising means comprises a camming surface fixedly disposed within the incubator above the holding means at the at-least one station, and a cam follower on the cap, the follower being positioned so that each follower encounters the camming surface and its cap is raised as the moving means moves the holding means and test elements through the at-least one station.

Accordingly, it is an advantageous feature of the invention that a simplified incubator is produced for analyzers using test elements that must be capped during incubation, for example, potentiometric test elements.

It is another advantageous feature of the invention that the size of such an incubator is substantially reduced.

A related advantageous feature of the invention is that fewer controls are needed for such an incubator, there being fewer active elements requiring such control.

Another related advantageous feature of the invention is improved reliability.

Other advantageous features will become apparent upon reference to the following description of the preferred embodiments, when read in light of the attached drawings.

DESCRIPTION OF THE PREFERRED EMBODIMENTS

The invention is described hereinafter with respect to the preferred embodiment that is a complete analyzer that uses dried test elements, and particularly one with separate loading and unloading stations and which can be used in zero-G environments. In addition, it is useful in any incubator, whether or not used as part of a complete analyzer, whether or not the test elements are "dried", whether or not the loading and unloading stations are separated or one station, and whether or not gravity is present, provided that caps for the test elements are used.

Descriptors such as "up", "down" and the like refer to orientations of use as they are shown in the attached drawings. As will be readily apparent, such orientations tend to be arbitrary if the apparatus is being described for use in zero gravity. Furthermore, the features of the invention will function also "upside down" in a 1-G environment.

Figure 1:
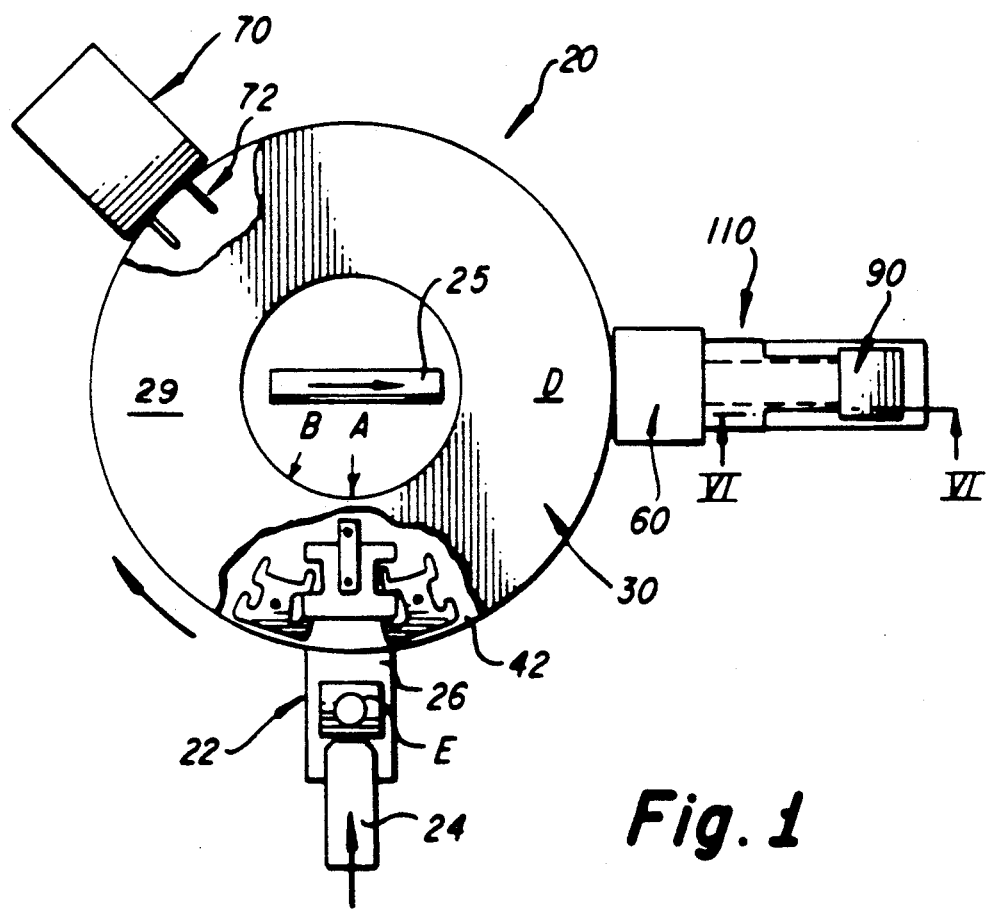
FIG. 1 is a partially broken away plan view of an analyzer using the incubator of the invention.

Referring to FIG. 1, an analyzer 20 constructed in accord with the invention comprises a sample-dispensing station 22, an incubator 30, means 24 for transferring test elements E containing patient sample, from station 22 into the incubator, a potentiometric read station 70 disposed adjacent to one side of incubator 30, a colorimetric read station 60, also disposed adjacent to the incubator and displaced circumferentially from read station 70, a container 90 to receive used test elements, a guide 110 to direct such used test elements from read station 60 to container 90, and transfer means 25 for transferring a test element from incubator 30 to read station 60 and then to guide 110 and container 90. Most preferably, transfer means 24 and 25 are pusher blades activated and guided in a conventional manner by motors, etc., not shown, moved over support surfaces such as surface 26. Guide 110 and container 90 can be conventional construction.

Considering first the conventional parts of the analyzer, any suitable liquid dispensing means (not shown) is useful at station 22. Such station 22 also includes suitable structure (not shown) that restricts test element E to movement generally in contact with surface 36, particularly when used in a zero-G environment.

Regarding potentiometric read station 70, FIG. 1, such station is conventional, and features a pair of electrodes 72 that raises and lowers into contact with appropriate parts of ISE test elements held by rotor 32. That station is not activated until an ISE test element is positioned thereunder, ready for reading, as controlled by a suitable microprocessor, not shown. (Detection of which kind of test element is at which indentation 34 is done by a bar code reader at station 22, not shown.)

Figure 5:
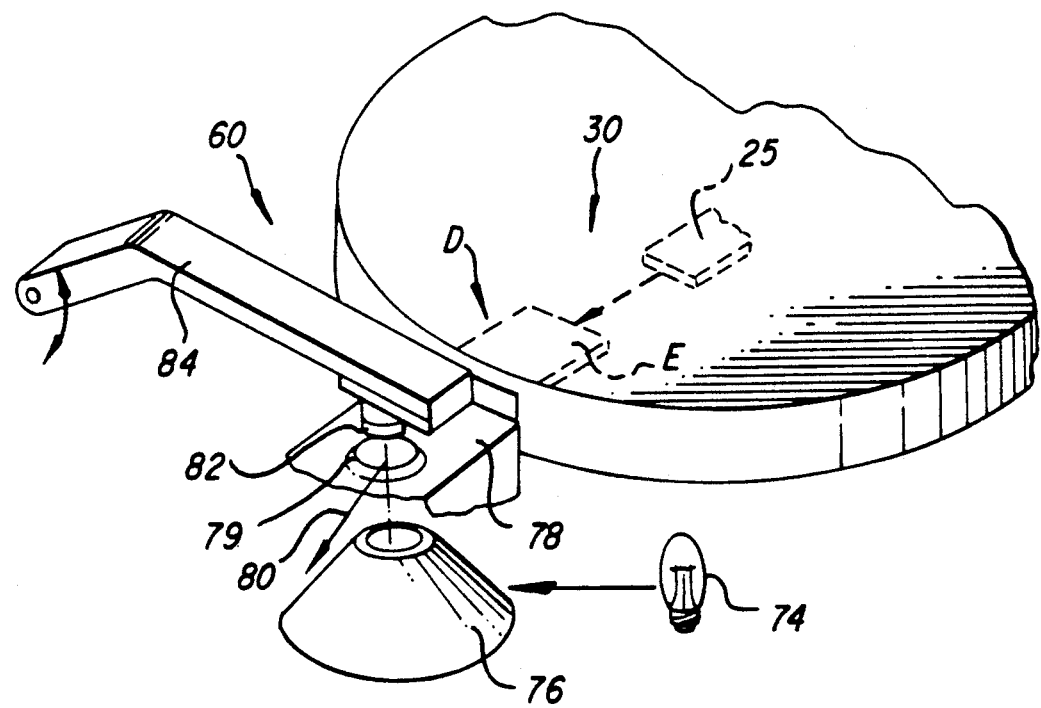
FIG. 5 is a fragmentary, partially schematic perspective view of the read station of the analyzer.

With respect to colorimetric read station 60, such station is conventional and features, FIG. 5, an appropriate light source 74 with optics, not shown, directing light to illuminating means 76, which is preferably an integrating surface, for example, the type disclosed in U.S. Pat. No. 4,660,984 (MacDonald). A support surface 78 is provided with a transparent window 79, over which a test element E is moved via appropriate pusher blades, such as blade 25. Light reflected from the element as beam 80 is then read via an appropriate detector, not shown. A cover 82 is positioned to hold element E in place for reading. Cover 82 is mounted on a raisable arm 84.

All test elements exit the incubator at station D, whether or not they are suitable for reading at read station 60. For those that are not (potentiometric test elements), read station 60 is simply inoperative.

Figure 3:
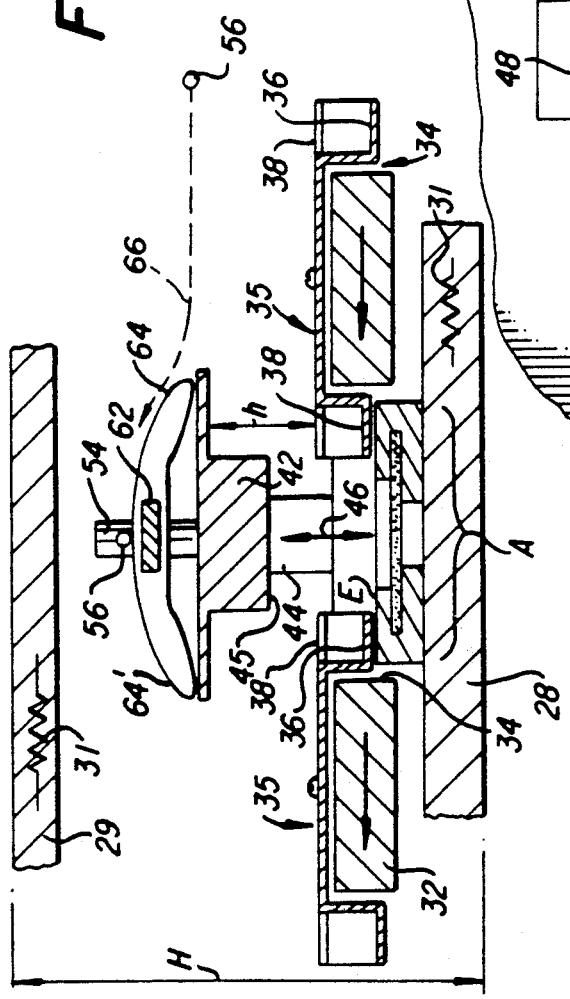
FIG. 3 is a section view taken generally along the line III—III of FIG. 2.
Figure 2:
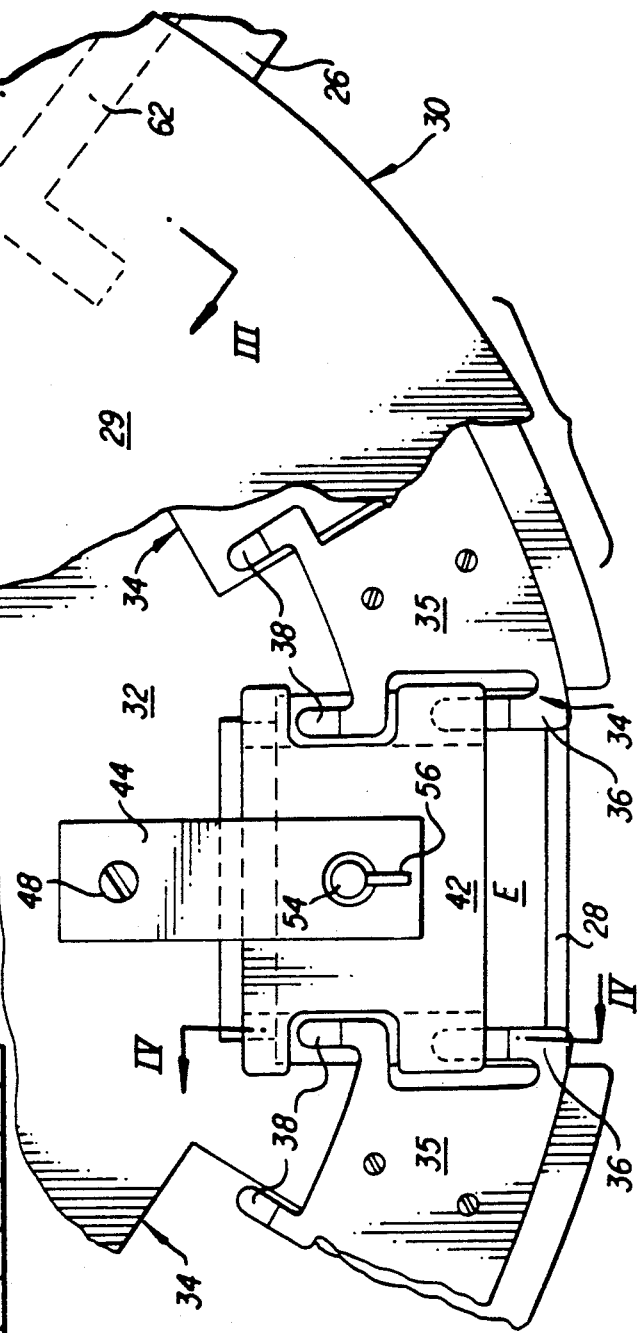
FIG. 2 is a fragmentary, enlarged plan view similar to that of FIG. 1, showing the incubator in greater detail.
Figure 4:
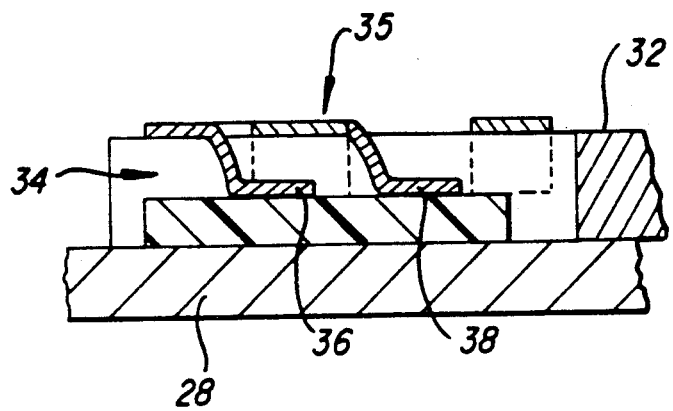
FIG. 4 is a fragmentary section view taken along the line IV—IV of FIG. 2.

Turning next to incubator 30, it comprises a stationary lower support plate 28, FIGS. 2-3, and a stationary upper cover plate 29. Either or both of these plates are heated by elements 31 in a conventional manner with sensors, not shown, to provide feedback to control the incubator temperature as desired. Mounted between plates 28 and 29, FIGS. 2 and 3, is a rotor 32 providing individual test-element holding stations formed as pockets in the rotor. More specifically, indentations 34 are formed in rotor 32, and hold-down leaf springs 35 are attached along the periphery of each indentation. The indentations are shaped and sized to hold a test element E therein, and springs 35 are shaped to press a test element against lower support plate 28, FIGS. 3 and 4. Preferably, springs 34 are dual springs that extend over the top of rotor 32, with a pair of fingers 36, 38 adjacent each indentation 34. Additionally, an evaporation cap 42 is provided, FIGS. 2 and 3, that is attached via a leaf spring 44 to rotor 32 to permit limited vertical movement, FIG. 3, arrow 46, of cap 42. Spring 44 is attached at 48 to rotor 32. Preferably, cap 42 is not attached to the spring but rather cap 42 is trapped between spring 44 and rotor 32. Undersurface 45 of cap 42 seals against test elements E.

In accord with the invention, means are provided for raising cap 42 against the action of spring 44 in a passive, rather than active way, simply by moving rotor 32 either into load station A or unload station D, FIG. 1. More specifically, FIGS. 2 and 3, each cap 42 has a rod 54, and projecting from rod 54 a cam follower pin 56 that functions as described below.

To raise cap 42 when rotor 32 moves an indentation 34 on plate 28 to station A to receive a test element, FIGS. 2 and 3, cam 58 is provided at station A, shown in phantom in FIG. 2. Cam 58 comprises a fixed bridge element 62 fixed to the analyzer and having an arcuate ramp surface 64. The shape of surface 64 is constructed to cam pin 56 upward, and thus raise cap 42, as shown by arrow 66, FIG. 3. Surface 64 spans the load station A, FIG. 3, and is fixed in place between the upper and lower heated plates 28 and 29. Distance "h" that cap 42 is raised is the distance sufficient for moving a test element into or out of place at indentation 34, without causing liquid protruding from the element from striking undersurface 45 of cap 42. For example, distance "h" can be 4 mm. The same is true regardless whether test element E is a potentiometric or colorimetric element.

When pin 56 traverses down the "down" side 64' of surface 64, cap 42 is lowered back into sealing contact with test element E, by reason of spring 44.

The construction of cam 58 at station D (not shown) is substantially identical with its construction at station A.

As a result of the use of this invention, the total height of the incubator is drastically reduced, the raising means taking up much less than the total height H, FIG. 3. Furthermore, the raising means is totally passive, requiring no control means to activate an active element, thereby simplifying the construction considerably.

The invention has been described in detail with particular reference to preferred embodiments thereof, but it will be understood that variations and modifications can be effected within the spirit and scope of the invention.

What is claimed is:

1. In an incubator, for use in a chemical analyzer and having a plurality of stations for holding a slide test element, each of said stations including a cap and means for biasing said cap onto a test element at said each station, raising means for raising said cap to allow entry or removal of a test element, and moving means for moving said stations past said raising means;

the improvement wherein said raising means comprises a camming surface fixedly disposed within said incubator above said caps, and a cam follower on each of said caps positioned so that each of said followers encounters said camming surface and its cap is raised as said moving means moves said biasing means and test elements past said raising means, so that the height of the incubator is minimized.

2. An incubator as defined in claim 1, wherein said raising means is free of active components requiring separate activation.

3. In an incubator for use with dried, slide test elements in a chemical analyzer, the test element containing a liquid for analysis, the incubator including means defining a plurality of stations in the incubator, including at least one station being constructed to provide a loading or an unloading function of a slide test element;

holding means at each of said stations for holding a plurality of test elements, means for moving said holding means and said slide test elements through said stations;

a plurality of movable evaporation caps disposed so that a cap is adjacent each of said stations, said caps being constructed to cover at least a portion of a test element at each station so as to prevent liquid evaporation, said caps including a spring mounted to bias said cap against a held test element; and means for raising said caps against said spring to allow entry or removal of a test element into or from said holding means;

the improvement wherein said raising means comprises a camming surface fixedly disposed within said incubator above said holding means at said at least one station, and a cam follower on each of said caps, said followers being positioned so that each of said followers encounters said camming surface and its cap is raised as said moving means moves said holding means and test elements through said at least one station, so that the height of the incubator is minimized.

4. An incubator as defined in claim 3, wherein said camming surface is an arcuate surface fixedly disposed a predetermined distance above said spring means and spanning said at least one station, said distance being sufficient to raise said caps enough to allow entry or removal of test elements.

5. An incubator as defined in claim 3, and further including opposed stationary surfaces having within them, members for heating the incubator; said caps being confined for movement between said surfaces.

6. In an analyzer for determining analytes in a liquid, said analyzer including a dispensing station for dispensing liquid onto a test element, an incubator for incubating test elements containing the liquid, and a read station for the incubated test elements;

the improvement wherein said incubator is an incubator as defined in claim 3.

* * * * *

UNITED STATES PATENT OFFICE
CERTIFICATE OF CORRECTION

PATENT NO. : 5,034,191
DATED : 23JUL91
INVENTOR(S) : Johannes J. Porte

Page 1 of 2

It is certified that error appears in the above-identified patent and that said Letters Patent is hereby corrected as shown below:

Cols. 5 and 6 should read:  --can be effected within the spirit and scope of the invention.

What is claimed is:

1. In an incubator for use with dried, slide test elements in a chemical analyzer, the test element containing a liquid for analysis, the incubator including
means defining a plurality of stations in the incubator, including at least one station being constructed to provide a loading or an unloading function of a slide test element;
holding means at each of said stations for holding a plurality of test elements,
means for moving said holding means and said slide test elements through said stations;
a plurality of movable evaporation caps disposed so that a cap is adjacent each of said stations, said caps being constructed to cover at least a portion of a test element at each station so as to prevent liquid evaporation, said caps including a spring mounted to bias said cap against a held test element; and
means for raising said caps against said spring to allow entry or removal of a test element into or from said holding means;
the improvement wherein said raising means comprises a camming surface fixedly disposed within said incubator above said holding means at said at least one station, and a cam follower on each of said caps, said followers being positioned so that each of said followers encounters said camming surface and its cap is raised as said moving means moves said holding means and test elements through said at least one station, so that the height of the incubator is minimized.

2. An incubator as defined in claim 1, wherein said camming surface is an arcuate surface fixedly disposed a predetermined distance above said spring means and spanning said at least one station, said distance being sufficient to raise said caps enough to allow entry or removal of test elements.

3. An incubator as defined in claim 1, and further including opposed stationary surfaces having within them, members for heating the incubator; said caps being confined for movement between said surfaces.

4. An incubator as defined in claim 1, wherein said raising means is free of active components requiring separate activation.

5. In an analyzer for determining analytes in a liquid, said analyzer including a dispensing station for dispensing liquid onto a test element, an incubator for incubating test elements containing the liquid, and a read station for the incubated test elements;
the improvement wherein said incubator is an incubator as defined in claim 1.

6. In an incubator, for use in a chemical analyzer and having a plurality of stations for holding a slide test element, each of said stations including a cap and means for biasing said cap onto a test element at said each station, raising means for raising said cap to allow entry or removal of a test element, and moving means for moving said stations past said raising means;
the improvement wherein said raising means comprises a camming surface fixedly disposed within said incubator above said caps, and a cam follower on each of said caps positioned so that each of said followers encounters said camming surface and its cap is raised as said moving means moves said biasing means and test elements past said raising means,
so that the height of the incubator is minimized.--

Signed and Sealed this

Ninth Day of February, 1993

*Attest:*

STEPHEN G. KUNIN

*Attesting Officer*  Acting Commissioner of Patents and Trademarks